(12) United States Patent
Cranch

(10) Patent No.: US 10,495,610 B2
(45) Date of Patent: Dec. 3, 2019

(54) FIBER OPTIC ACOUSTIC EMISSION SENSOR AND APPARATUS

(71) Applicant: GOVERNMENT OF THE UNITED STATES OF AMERICA, AS REPRESENTED BY THE SECRETARY OF THE NAVY, Arlington, VA (US)

(72) Inventor: Geoffrey A. Cranch, Fairfax Station, VA (US)

(73) Assignee: Geoffrey A. Cranch, Washington, DC (US)

( * ) Notice: Subject to any disclaimer, the term of this patent is extended or adjusted under 35 U.S.C. 154(b) by 123 days.

(21) Appl. No.: 15/676,098

(22) Filed: Aug. 14, 2017

(65) Prior Publication Data

US 2019/0049412 A1 Feb. 14, 2019

(51) Int. Cl.
*G01N 29/14* (2006.01)
*G01N 29/24* (2006.01)
*G01H 9/00* (2006.01)
*G01N 29/26* (2006.01)

(52) U.S. Cl.
CPC ............ *G01N 29/14* (2013.01); *G01H 9/004* (2013.01); *G01N 29/2418* (2013.01); *G01N 29/2425* (2013.01); *G01N 29/262* (2013.01); *G01N 2291/014* (2013.01); *G01N 2291/0258* (2013.01)

(58) Field of Classification Search
CPC .... G01N 29/14; G01N 29/2418; G01H 9/004; G02B 6/34; G02B 6/02076; G01L 11/025; G01L 1/246; G01L 1/242
See application file for complete search history.

(56) References Cited

U.S. PATENT DOCUMENTS

| | | | | |
|---|---|---|---|---|
| 5,867,258 A | * | 2/1999 | Frederick | G01H 9/004 250/227.27 |
| 6,597,821 B1 | * | 7/2003 | Bohnert | G01F 1/44 385/12 |
| 6,630,658 B1 | * | 10/2003 | Bohnert | G01L 11/025 250/227.14 |
| 7,017,421 B2 | * | 3/2006 | Kehlenbach | G01L 1/165 73/800 |
| 7,030,366 B2 | * | 4/2006 | Seeley | G01B 11/18 250/227.14 |

(Continued)

OTHER PUBLICATIONS

Read, et al., Optical Fibre Acoustic Emission Sensor for Damage Detection in Carbon Fibre Composite Structures, Meas. Sci. Technol., Dec. 4, 2001, pp. N5-N9, vol. 13, Issue 1, Institute of Physics Publishing, UK.

(Continued)

*Primary Examiner* — Helen C Kwok
(74) *Attorney, Agent, or Firm* — US Naval Research Laboratory; Suresh Koshy

(57) ABSTRACT

A method of monitoring a structure for stresses or cracks. A single mode optical fiber is adhered to a structure. The single mode optical fiber includes a first optical cavity. The first optical cavity includes two fiber Bragg gratings with a distance therebetween. The first optical cavity includes a resonance. A frequency shift of the resonance of the first optical cavity is measured with a frequency discriminator. An acoustic emission from the structure is detected based on the frequency shift.

22 Claims, 16 Drawing Sheets

(56) References Cited

U.S. PATENT DOCUMENTS

| | | | |
|---|---|---|---|
| 7,684,112 B2* | 3/2010 | He | G02F 1/3526 359/326 |
| 2001/0013934 A1* | 8/2001 | Varnham | G01D 5/35383 356/478 |
| 2004/0093950 A1* | 5/2004 | Bohnert | G01L 11/025 73/705 |
| 2006/0011820 A1* | 1/2006 | Chow-Shing | A61B 5/01 250/227.14 |
| 2009/0157358 A1* | 6/2009 | Kim | G01L 1/16 702/185 |
| 2010/0326200 A1* | 12/2010 | Sheverev | G01B 11/165 73/800 |
| 2011/0019179 A1* | 1/2011 | Molin | G01D 5/35303 356/32 |
| 2013/0090867 A1* | 4/2013 | Strong | G01M 3/002 702/51 |
| 2013/0272645 A1* | 10/2013 | Cranch | G02B 6/34 385/12 |
| 2014/0252210 A1* | 9/2014 | Schmidt | G01K 11/32 250/208.2 |
| 2016/0116366 A1* | 4/2016 | Da Silva | G01M 5/0033 702/35 |
| 2017/0234837 A1* | 8/2017 | Hall | B06B 3/00 73/602 |
| 2018/0299301 A1* | 10/2018 | Raghavan | G01D 5/35351 |
| 2019/0006157 A1* | 1/2019 | O'Banion | H01L 21/67109 |

OTHER PUBLICATIONS

Chen, et al., Fiber Optic Acoustic Emission Distributed Crack Sensor for Large Structures, Journal of Structural Control, Jun. 1, 2000, pp. 119-129, vol. 7 N, John Wiley & Sons, Inc., U.S.

Slavik, et al., Short Multiwavelength Fiber Laser Made of a Large-Band Distibuted Fabry-Perot Structure, IEEE Photonics, Technology Letters, Apr. 4, 2004, pp. 1017-1019, vol. 16, No. 4, IEEE, US.

* cited by examiner

FIBER OPTIC ACOUSTIC EMISSION SENSOR AND APPARATUS

FIELD OF THE INVENTION

The present invention relates in general to a method of monitoring structural health, and in particular to a method of measuring ultrasonic signals caused by acoustic emission for structural health monitoring.

BACKGROUND OF THE INVENTION

Effective structural health monitoring ("SHM") systems require large numbers of miniature, lightweight sensors capable of measuring a range of parameters. Fiber optic sensors are a promising technology to provide this measurement capability with large numbers of sensors multiplexed onto a single fiber capable of measuring of strain, temperature and ultrasonics. Fiber optic sensors provide a minimally invasive sensing capability with a greatly reduced number of interconnects and cabling, which is expected to lead to greatly improved system reliability. For example, multiplexed arrays of fiber Bragg grating sensors are capable of measuring slowly varying strain with a performance that matches existing conventional piezoelectric strain gauges (<1 microstrain).

There is also interest in measuring high frequency signals generated either by structural fatigue through crack formation, in the form of acoustic emission ("AE"), as well as actively generated signals such as Lamb waves generated by piezoelectric sources for damage detection. Piezoelectric sensor performance can be tailored in terms of their size, response and electronic amplification circuitry to provide the required performance for a given application; however, these sensors are large and are not practical to be implemented in large numbers.

BRIEF SUMMARY OF THE INVENTION

An embodiment of the invention includes use of a fiber laser acoustic emission sensor. Such a sensor provides extremely high sensitivity required for passive AE measurement, whilst being capable of integration with strain and temperature sensors. Such an embodiment of the invention measures ultrasonic signals caused by acoustic emission in structures using fiber laser strain sensors. For example, sources of acoustic emission include all ultrasonic signals generated from the joints associated with fretting and rubbing of the materials as well as the crack signals generated from material fatigue. In addition, this embodiment of the invention measures Lamb wave signals generated from other sources of acoustic emission, such as piezoelectrics and laser induced ultrasound.

An embodiment of the invention includes integrating sensors into shallow groves or channels made in panels or structures to perform acoustic emission measurements without introducing structural weakness or fatigue into the structure.

An embodiment of the invention includes a method and is described as follows. A standard single mode optical fiber is adhered to a standard structure. The single mode optical fiber includes a first optical cavity. The first optical cavity includes two fiber Bragg gratings with a distance therebetween. The first optical cavity includes a resonance. A frequency shift of the resonance of the first optical cavity is detected or measured with a frequency discriminator. An acoustic emission from the structure is detected based on the frequency shift.

Another embodiment of the invention includes a method, and is described as follows. A single mode optical fiber is adhered to a structure. The single mode optical fiber includes a plurality of optical cavities tuned to respective optical frequencies. Each optical cavity of the plurality of optical cavities includes two fiber Bragg gratings with a distance therebetween. Each optical cavity of the plurality of optical cavities includes a respective resonance. The structure includes an acoustic wavelength. A respective frequency shift is detected or measured for each respective resonance with a frequency discriminator. A plurality of respective acoustic emissions from the structure is detected. Each respective acoustic emission of the plurality of acoustic emissions is based on each respective frequency shift. A direction of an acoustic emissions source is determined by applying standard phased array processing to the plurality of respective acoustic emissions. Optionally, the single mode optical fiber includes a standard optical gain medium. The optical gain medium is excited using a standard optical pump, thereby generating lasing in the optical cavity. Optionally, the optical gain medium includes an erbium-doped optical gain medium or a neodymium-doped optical gain medium.

An embodiment of the invention advantageously uses lightweight components, which are easily integrated into a structure to be monitored for strains and stresses.

An embodiment of the invention has a wide bandwidth, e.g., greater than 100 kHz.

An embodiment of the invention advantageously facilitates the multiplexing of multiple sensors, which in turn makes phased array beam forming possible. Such phased array beam forming provides the location of an acoustic emission event. Advantageously, such phased array beam forming rejects background noise (or clutter). Examples of such acoustic emission events include cracks in fatigued lap joints. Once the location is known, standard remedial steps are taken by caretakers of the structure. Such remedial steps include standard repair or standard replacement of the structure.

DETAILED DESCRIPTION OF THE INVENTION

Figure 1:
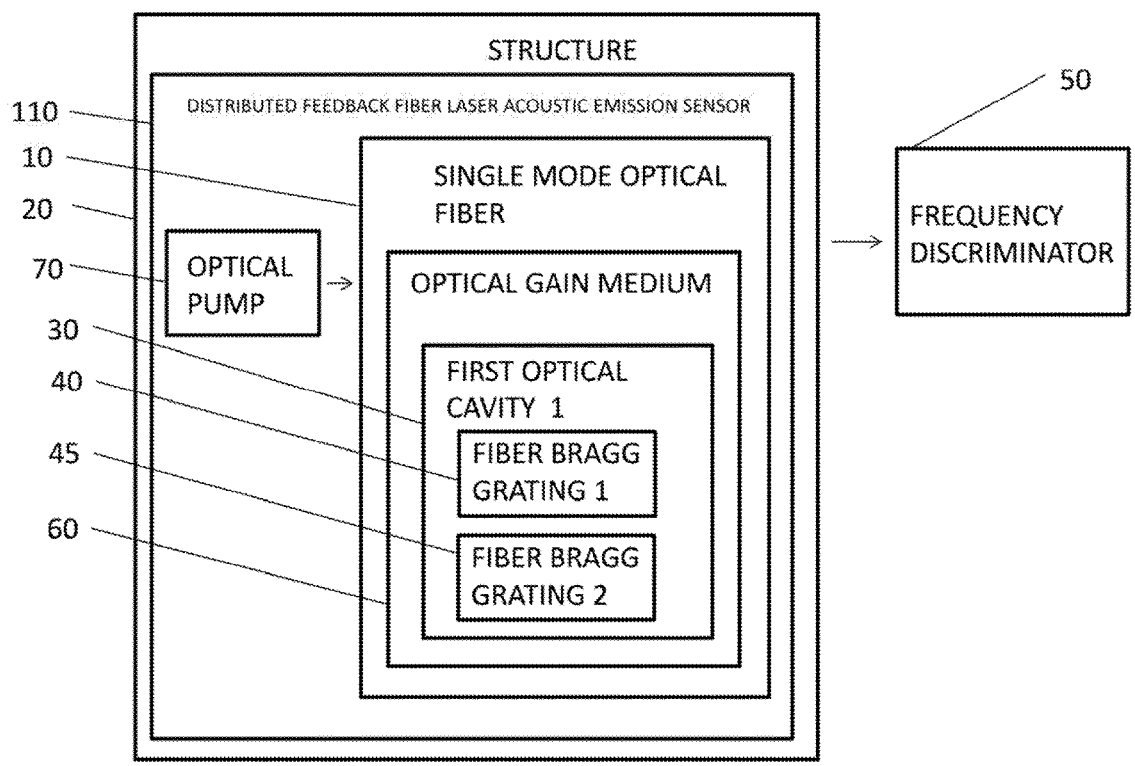
FIG. 1 is a block diagram including elements required to practice an embodiment of the invention.

An embodiment of the invention includes a method and is described as follows. As shown by way of illustration in FIG. 1, a standard single mode optical fiber 10 is adhered to a standard structure 20. Such structures 20 include standard materials, including standard metal, standard wood, standard glass, standard plastic, and/or standard composites thereof. Such structures 20 include, for example, structures with flat surfaces 22 or structures with curved surfaces 24, such as shown in FIGS. 5-10. Examples of such standard structures 20 include standard stationary structures, such as standard buildings. Examples of such buildings include standard commercial facilities, standard government facilities, standard residential facilities, and standard facilities in geographically remote or hostile areas, and standard unmanned facilities. Examples of structures consistent with an embodiment of the invention also include standard moveable structures, such as standard land vehicles, standard watercraft, and standard aircraft. Examples of such standard watercraft include ships. Examples of such standard aircraft include standard commercial airplanes, standard government airplanes, and standard private airplanes. Damage in these structures occurs from the formation of cracks which generate bursts of ultrasonic energy, commonly known as acoustic emission. This acoustic emission can be measured directly as a means of detecting when cracks occur. Alternatively, the presence of a crack may be determined by generating an ultrasonic signal from a standard piezoelectric sensor attached to the structure 20. The signal from the piezoelectric sensor is scattered by the crack and the scattered signal is measured with the fiber laser sensor. In thin materials (e.g. less than 20 mm thick), this mechanical energy will propagate in the form of a Lamb wave. In thicker materials, this energy may propagate as a bulk acoustic wave. The single mode optical fiber 10 includes a standard, first optical cavity 30, as shown by way of illustration in FIGS. 1-4. The first optical cavity 30 includes two, standard, fiber Bragg gratings 40, 45 with a distance therebetween. The first optical cavity 30 includes a resonance. A frequency shift of the resonance of the first optical cavity 30 is detected or measured with a standard frequency discriminator 50. An acoustic emission from the structure 20 is detected based on the frequency shift.

For the purpose of this specification and the following claims, acoustic emission refers to the generation of transient elastic waves produced by a sudden redistribution of stress in a structure. When the structure is subjected to aging or an external stimulus (e.g., a change in pressure, load, and/or temperature), localized sources trigger the release of energy, in the form of elastic waves (or stress waves), which propagate to the surface of the material.

Figure 16:
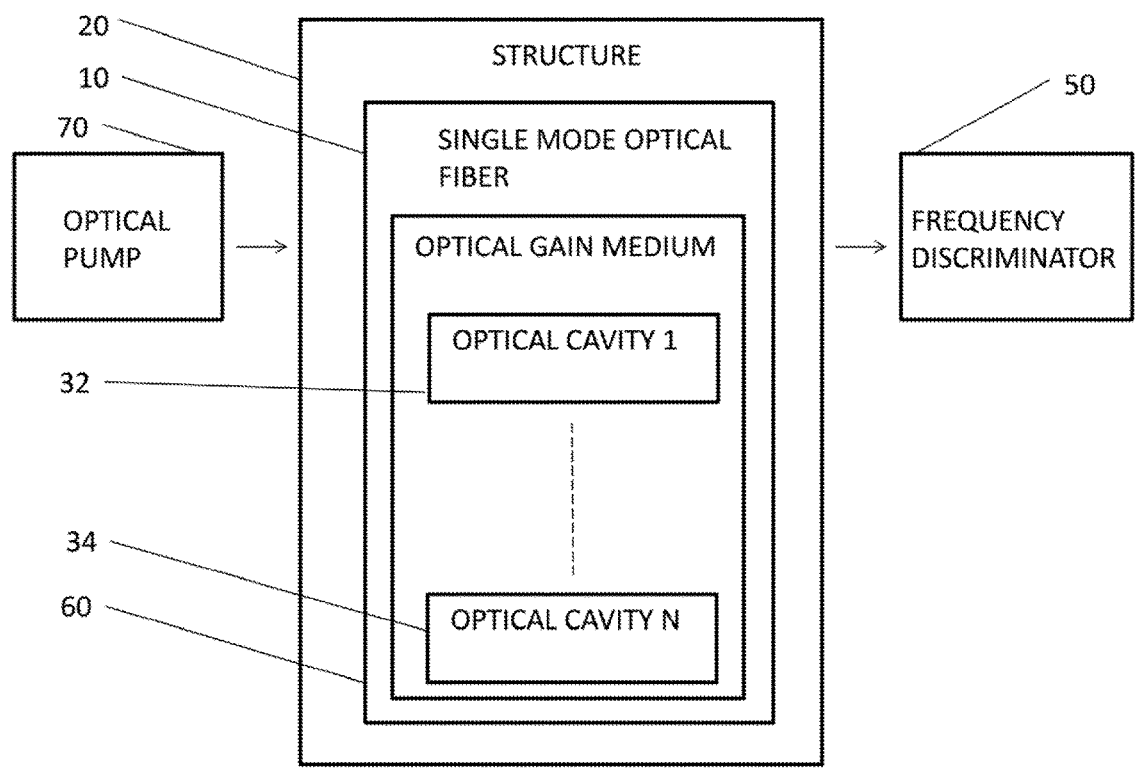
FIG. 16 is a block diagram including elements required to practice an alternative embodiment of the invention.

Optionally, the single mode optical fiber 10 includes a standard optical gain medium 60. The optical gain medium 60 is excited using a standard optical pump 70, thereby generating lasing in the optical cavity 30. In an embodiment of the invention, the optical pump 70 is local to the structure 20, such as shown in FIG. 1. In another embodiment of the invention, the optical pump 70 is remote from the structure 20, such as shown in FIG. 16. Optionally, the optical gain medium 60 includes a standard rare-earth doped optical gain medium. For example, the optical gain medium 60 includes a standard erbium-doped optical gain medium 62, as shown by way of illustration in FIG. 3, or a standard neodymium-doped optical gain medium 64, as shown by way of illustration in FIG. 4.

Optionally, the optical pump 70 includes an optical wavelength. The first optical cavity 30 includes an optical cavity width. For example, the optical cavity width is about a multiple of half of the optical wavelength to satisfy the standing wave condition. For example, the optical cavity width is about one half of the optical wavelength. For example, an optical cavity width appropriate for an optical wavelength of 1550 nm is 775 nm. One of ordinary skill in the art will readily appreciate that the optical cavity width is optionally greater than or less than exactly half of the optical wavelength. However, as deviations from half of the optical wavelength become greater and greater, amplification in the optical cavity becomes increasingly impaired because of greater and greater destructive interference. Accordingly, for example, an optical cavity width within 25% of a multiple of half of the optical wavelength is preferred. For example, an optical cavity width within 25% of half of the optical wavelength is preferred.

Optionally, adhering a single mode optical fiber 10 to the structure 20 includes using a standard viscoelastic substance 80 to impedance-match the single mode optical fiber to the structure, such as shown in FIGs. For example, such a standard viscoelastic substance 80 includes a standard viscous liquid or a standard adhesive to impedance-match the single mode optical fiber to the structure. Optionally, the viscous liquid includes standard gel or standard grease or water. Optionally, a groove is made in the structure, and the single mode optical fiber 20 is put in the groove and sealed therein with the viscoelastic substance 80. One of ordinary skill in the art will readily appreciate that the depth of the groove should be shallow enough such that the groove itself does not introduce structural weakness or fatigue to the structure. One of ordinary skill in the art will also readily appreciate that the cross-sectional profile of the groove optionally depends on the application and/or ease of manufacture. For example, the groove is a standard V-shaped groove 92, as shown by way of illustration in FIGS. 5 and 6. For example, the groove is a standard rectangular groove 94, as shown by way of illustration in FIGS. 7 and 8. For example, the groove is a standard U-shaped groove 96, as shown by way of illustration in FIGS. 9 and 10.

Optionally, adhering a single mode optical fiber 10 to the structure 20 includes enclosing the single mode optical fiber in a standard viscous-liquid-filled tube 100. Optionally, the viscous-liquid-filled tube 100 includes a standard plastic tube, a standard polytetrafluoroethylene tube, or a standard polyvinyl chloride tube.

Figure 2:
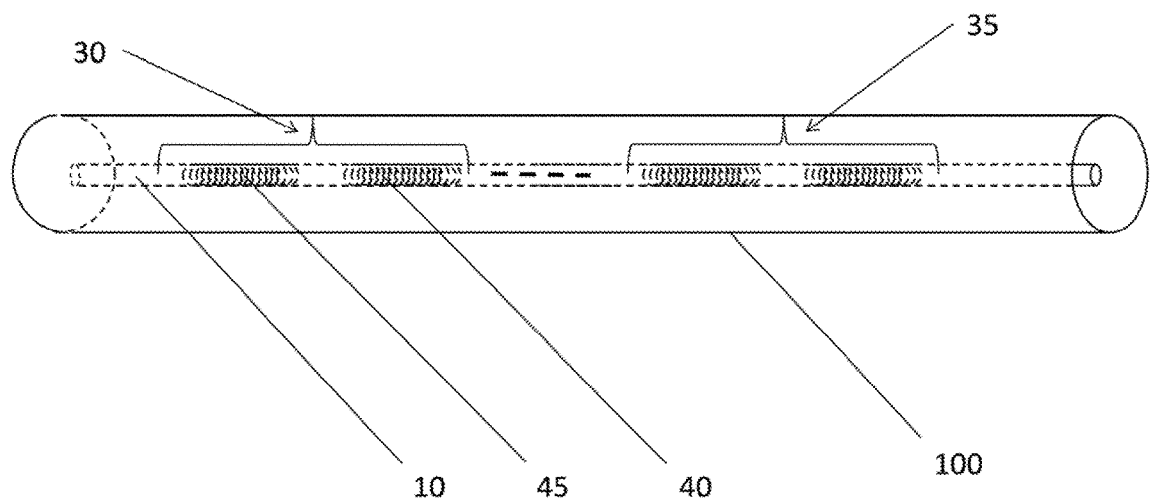
FIG. 2 is a perspective view of an illustrative single mode optical fiber for use in an embodiment of the invention.
Figure 3:
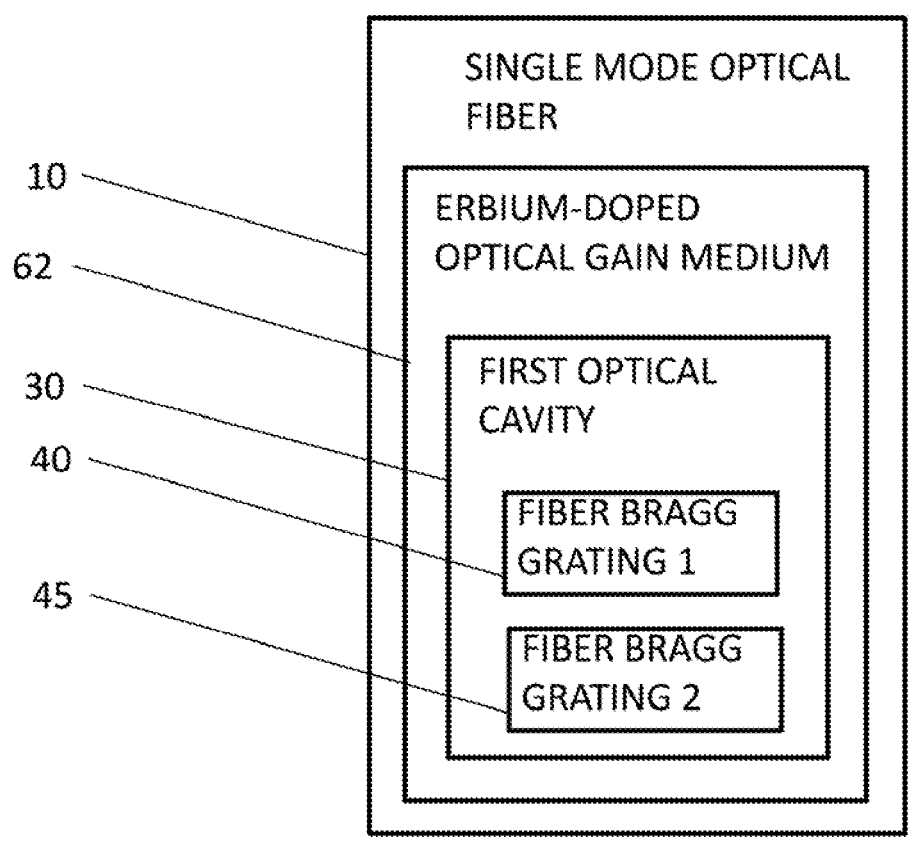
FIG. 3 is a block diagram of an illustrative single mode optical fiber for use in an embodiment of the invention.
Figure 4:
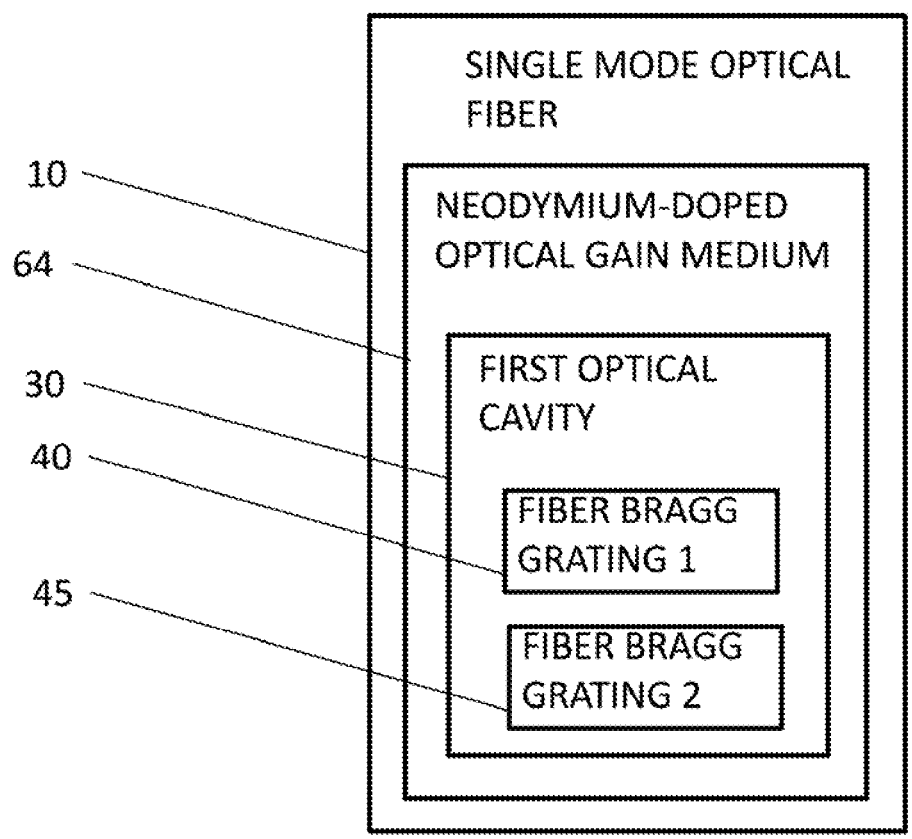
FIG. 4 is a block diagram of another illustrative single mode optical fiber for use in an embodiment of the invention.
Figure 5:
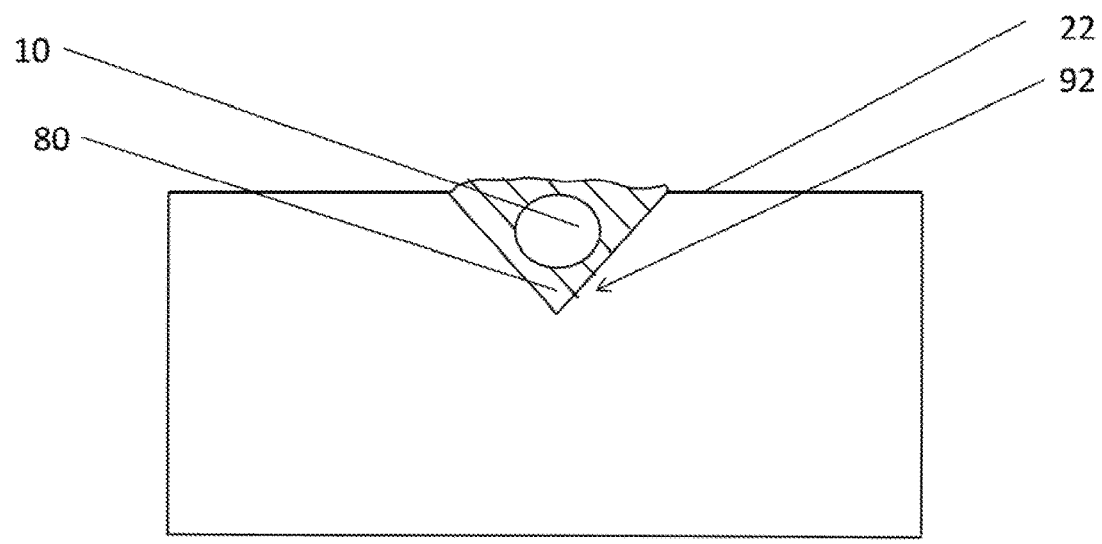
FIG. 5 is a cross-sectional view of an illustrative single mode optical fiber adhered to a V-shaped groove of an illustrative flat-surfaced structure to be monitored, as practiced in an embodiment of the invention.
Figure 6:
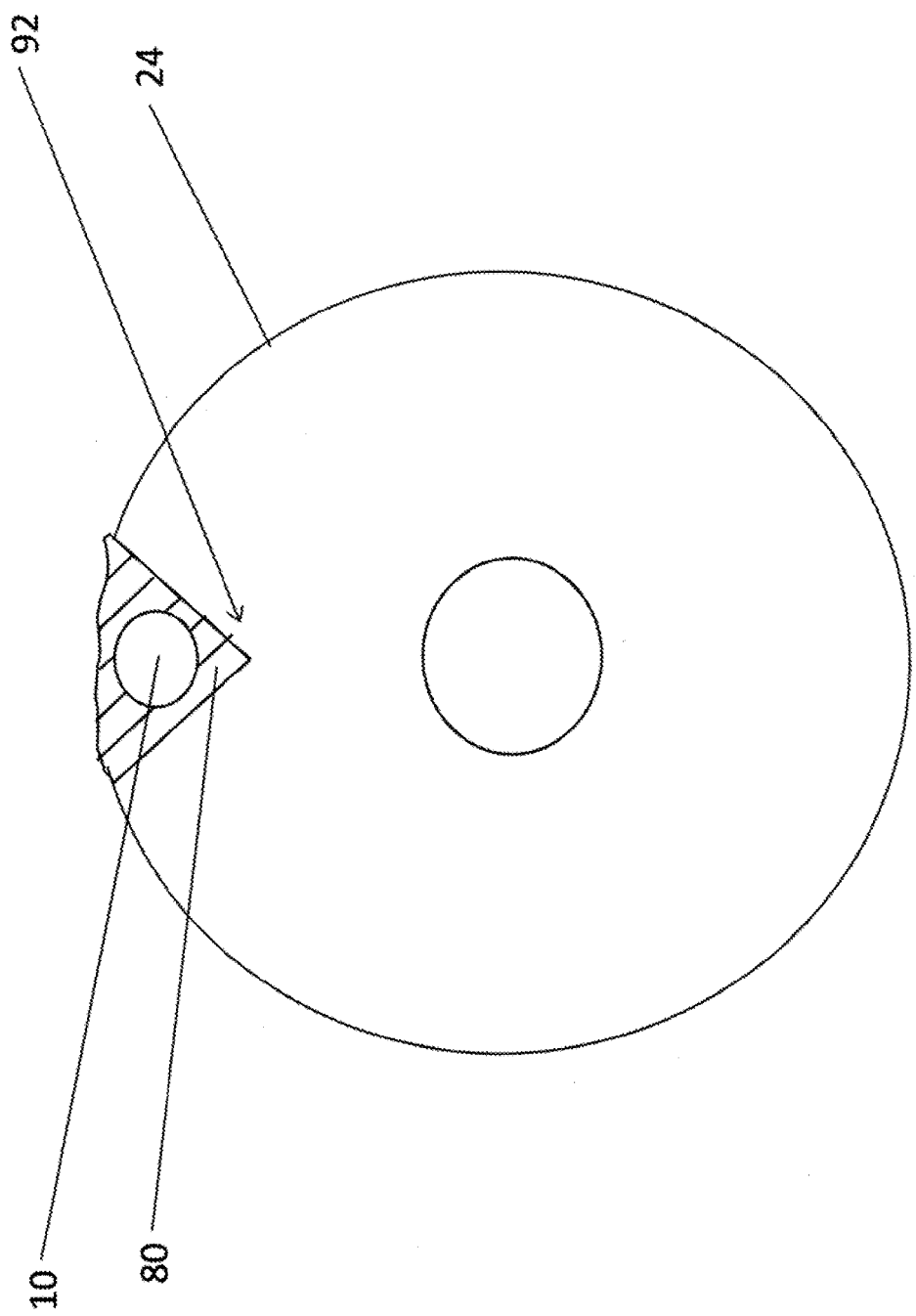
FIG. 6 is a cross-sectional view of an illustrative single mode optical fiber adhered to a V-shaped groove of a curved structure to be monitored, as practiced in an embodiment of the invention.
Figure 7:
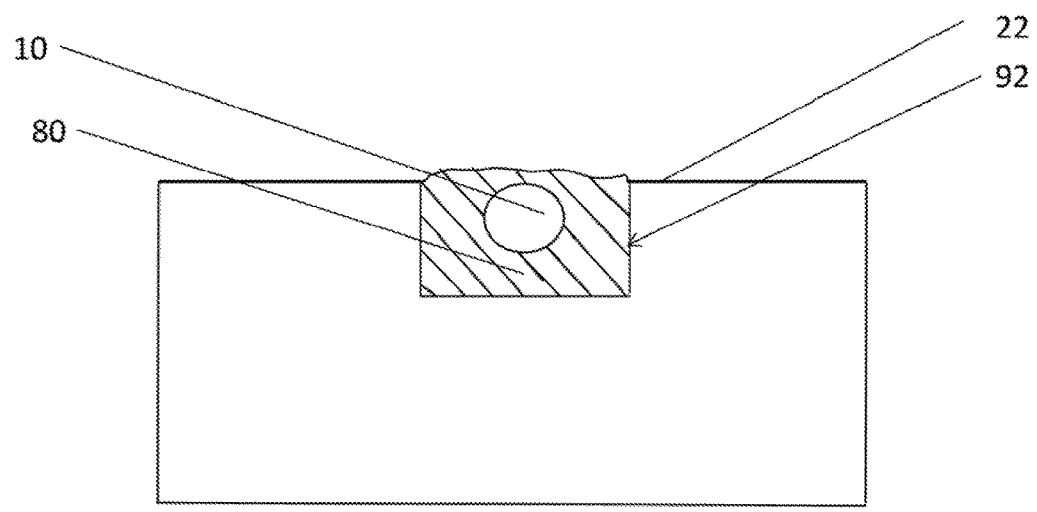
FIG. 7 is a cross-sectional view of an illustrative single mode optical fiber adhered to a rectangular-shaped groove of a structure to be monitored, as practiced in an embodiment of the invention.
Figure 8:
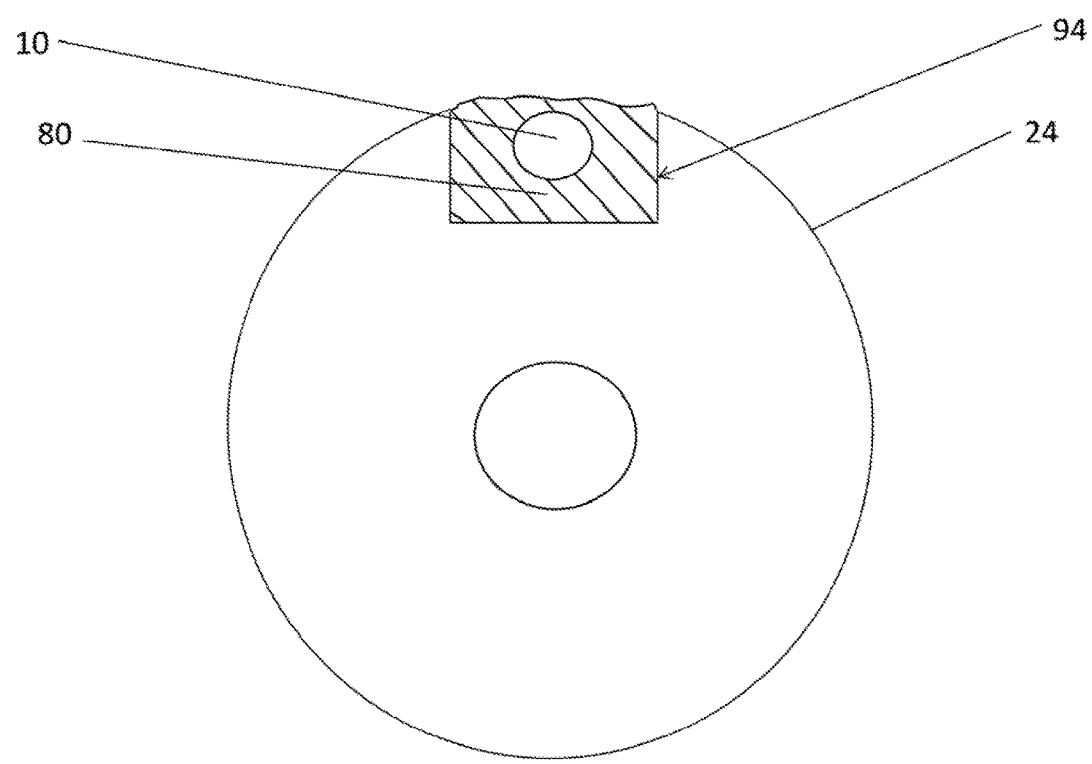
FIG. 8 is a cross-sectional view of an illustrative single mode optical fiber adhered to a rectangular-shaped groove of a structure to be monitored, as practiced in an embodiment of the invention.
Figure 9:
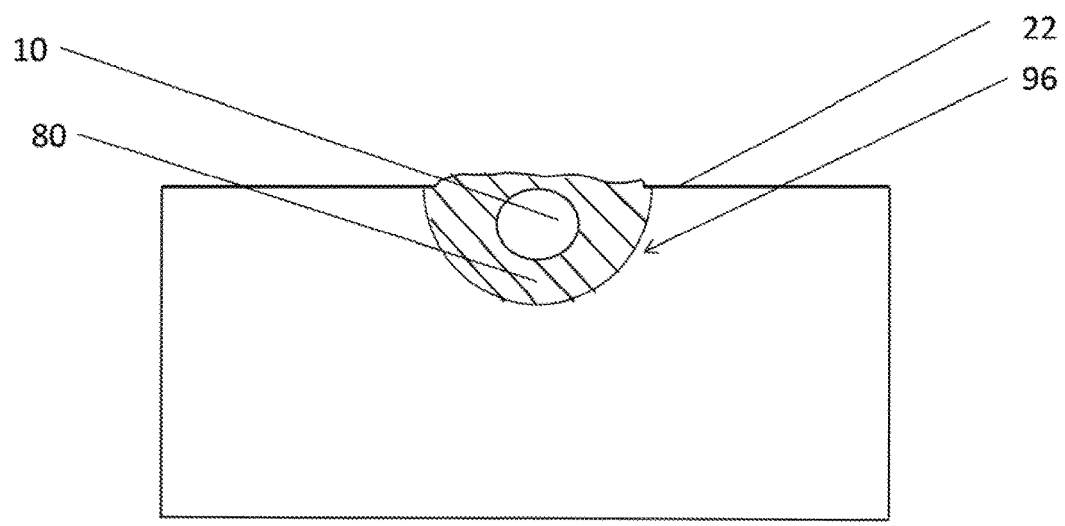
FIG. 9 is a cross-sectional view of an illustrative single mode optical fiber adhered to a U-shaped groove of a structure to be monitored, as practiced in an embodiment of the invention.
Figure 10:
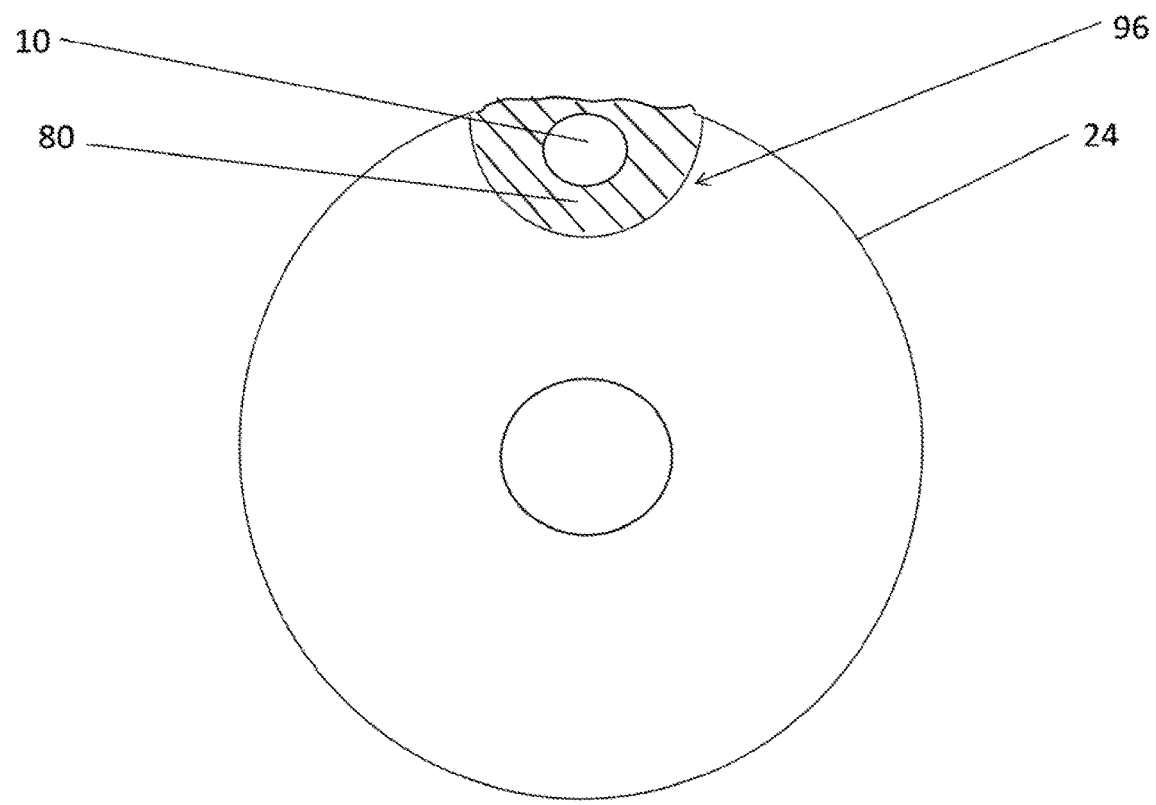
FIG. 10 is a cross-sectional view of an illustrative single mode optical fiber adhered to a U-shaped groove of a structure to be monitored, as practiced in an embodiment of the invention.

Optionally, the optical pump 70 includes a standard semiconductor laser, a standard laser diode, or a standard light emitting diode. Optionally, other embodiments of the invention include a standard multi-wavelength optical pump and two or more optical cavities with respective resonances corresponding to the optical pump's multiple wavelengths. For example, such two or more optical cavities include a series of optical cavities 1 to N with differing (e.g., sequentially increasing) wavelengths, as shown by way of illustration in FIG. 1. For ease of understanding, FIG. 2 shows only two optical cavities 30, 35, each including two fiber Bragg gratings. However, one of ordinary skill in the art will readily appreciate that for each desired laser mode, there is a corresponding optical cavity in the single mode optical fiber according to an embodiment of the invention. For example, in an embodiment of the invention, up to 50 laser modes are supported along a 10 cm length of a fiber Bragg gratings in a single mode optical fiber. For example, such multi-wavelength optical pumps include standard multi-wavelength fiber lasers. Such multi-wavelength fiber lasers, for example, include wavelengths of 1520 nm to 1560 nm.

Figure 11:
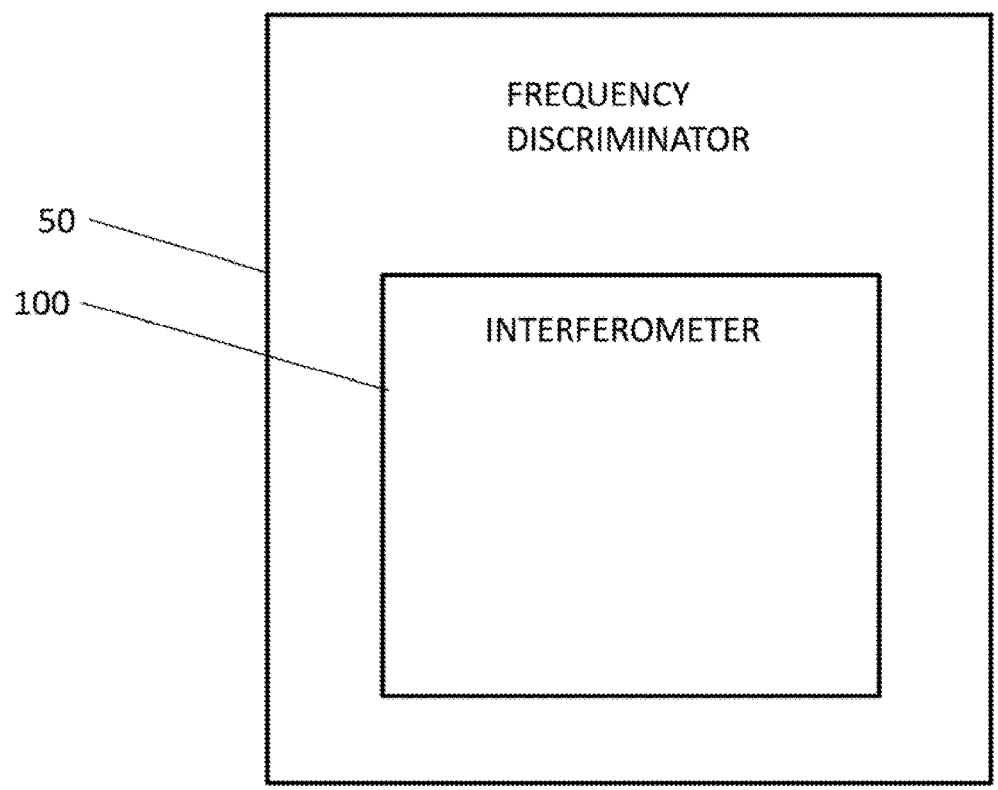
FIG. 11 is a block diagram of a frequency discriminator including an interterometer for use in an embodiment of the invention.
Figure 12:
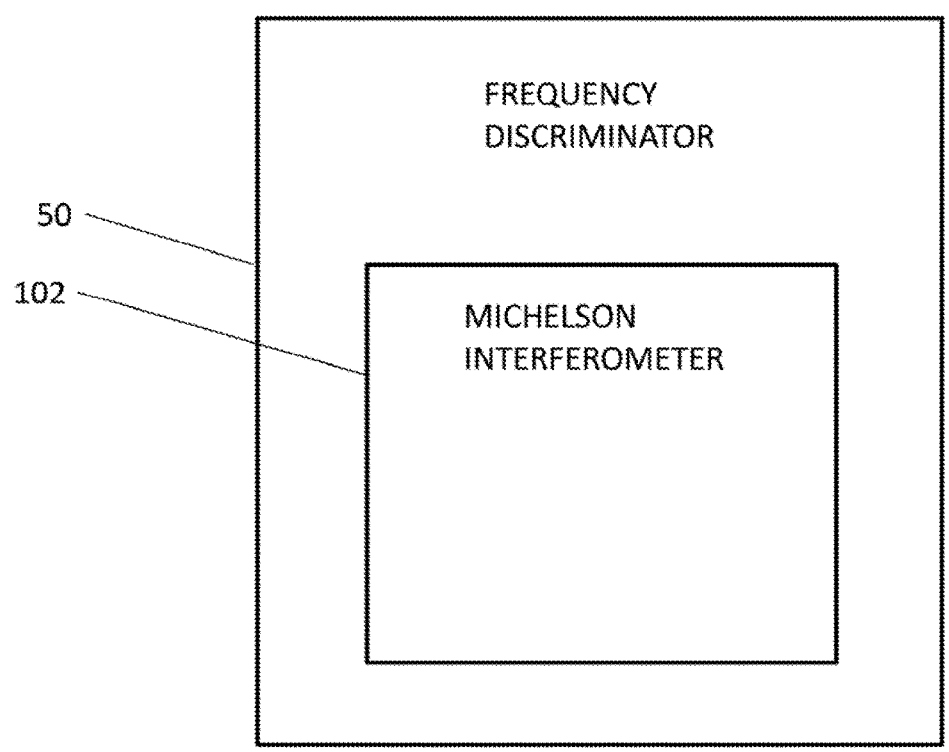
FIG. 12 is a block diagram of a frequency discriminator including a Michelson interferometer for use in an embodiment of the invention.
Figure 13:
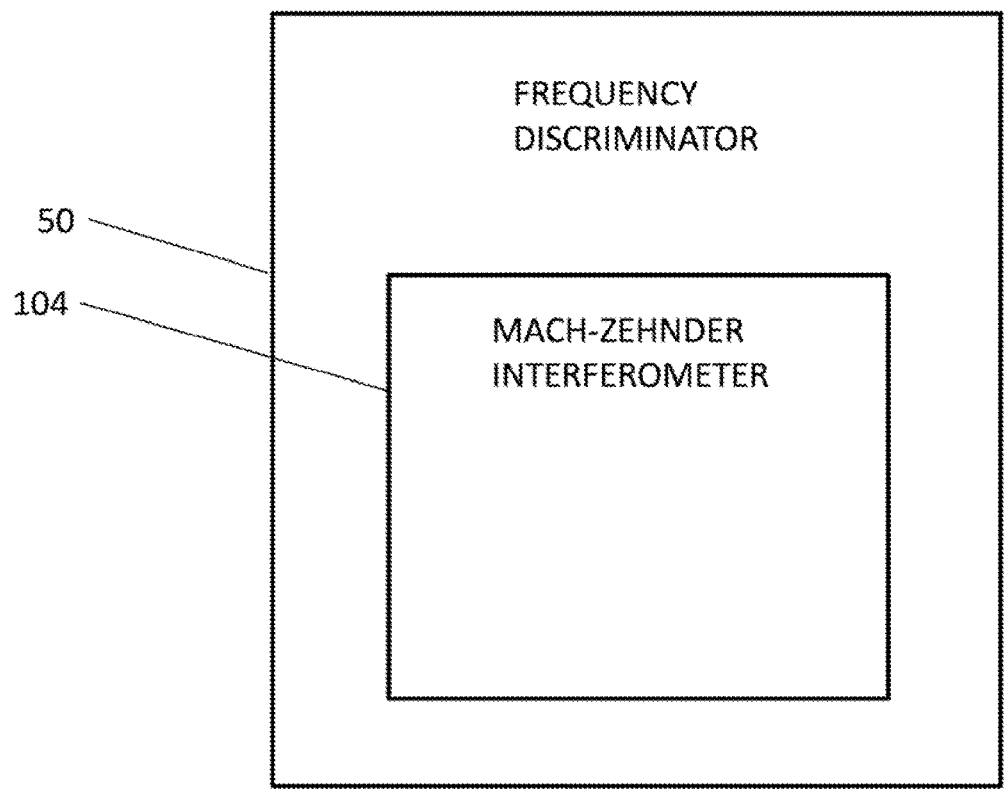
FIG. 13 is a block diagram of a frequency discriminator including a Mach-Zehnder interferometer for use in an embodiment of the invention.
Figure 14:
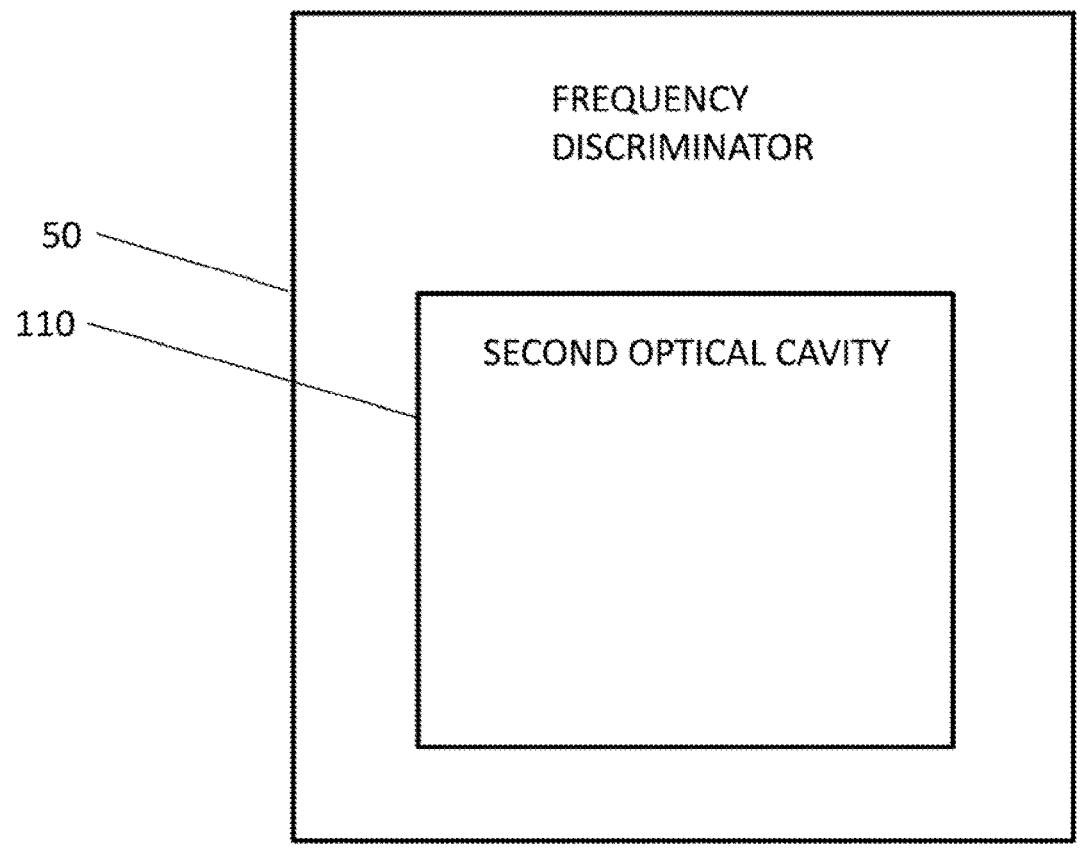
FIG. 14 is a block diagram of a frequency discriminator including a second optical cavity for use in an embodiment of the invention.
Figure 15:
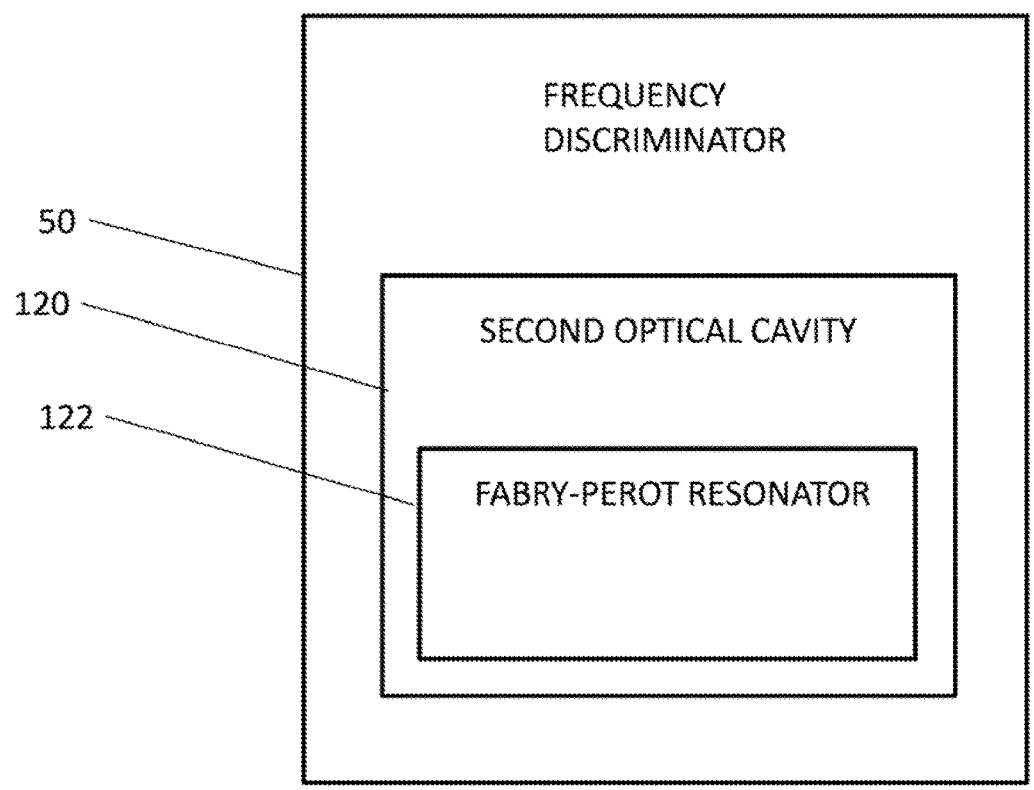
FIG. 15 is a block diagram of a frequency discriminator including a Fabry-Perot resonator for use in an embodiment of the invention.

Optionally, the frequency discriminator 50 includes a standard interferometer 100, as shown by way of illustration in FIG. 11, or a standard second optical cavity, as shown by way of illustration in FIG. 12. Optionally, the interferometer 100 includes a standard Michelson 102 interferometer, as shown by way of illustration in FIG. 13, or a standard Mach-Zehnder interferometer 104, as shown by way of illustration in FIG. 14. Optionally, the second optical cavity 120 includes a standard Fabry-Perot resonator 122, as shown by way of illustration in FIG. 15.

Optionally, a laser beam is transmitted from the optical pump 70 through the single mode optical fiber 10. The laser beam includes a laser beam frequency. The laser beam frequency is tuned to the resonance of the first optical cavity. Changes in the resonance of the first optical cavity are read out by the frequency discriminator 50 based on changes in transmitted or reflected laser beam from the first optical cavity.

Another embodiment of the invention includes a method, and is described as follows. A single mode optical fiber 10 is adhered to a structure 20, as shown by way of example in FIG. 16. The single mode optical fiber 10 includes a plurality of optical cavities 30, 35 tuned to respective optical frequencies. Each optical cavity of the plurality of optical cavities 30, 35 includes two fiber Bragg gratings 40, 45 with a distance therebetween. Each optical cavity of the plurality of optical cavities 30, 35 includes a respective resonance. The acoustic emission includes an acoustic wavelength and frequency. The separation between optical cavities is about half of the acoustic wavelength. For example, an optical cavity spacing appropriate for an acoustic wavelength of 100 kHz is about 2 cm. As another example, an optical cavity spacing appropriate for an acoustic wavelength of 1 MHz is about 2 mm. A respective frequency shift is detected or measured for each respective resonance with a standard frequency discriminator 50. A plurality of respective acoustic emissions from the structure 20 is detected. Each respective acoustic emission of the plurality of acoustic emissions is based on each respective frequency shift. A direction of an acoustic emissions source is determined by applying standard phased array processing to the plurality of respective acoustic emissions, such as discussed in Lukasz Ambrozinski, "Beamforming of guided waves" chapter 7 in Advanced Structural Damage Detection: From Theory to Engineering Applications, $1^{st}$ ed., Edn T. Stepinski, T. Uhl, W. Staszewski, John Wiley, 2013, incorporated herein by reference. Optionally, the single mode optical fiber 10 includes a standard optical gain medium 60. The optical gain medium 60 is excited using a standard optical pump 70, thereby generating lasing in the optical cavity. Optionally, the optical gain medium 70 includes an erbium-doped optical gain medium or a neodymium-doped optical gain medium.

Optionally, the distance between optical cavities is about half of the acoustic wavelength.

Optionally, adhering a single mode optical fiber to a structure includes using a standard viscous liquid or a standard adhesive to impedance-match the single mode optical fiber to the structure. Optionally, the viscous liquid includes standard gel or standard grease.

Optionally, adhering a single mode optical fiber to a structure includes enclosing the single mode optical fiber in a standard viscous-liquid-filled tube. Optionally, the viscous-liquid-filled tube includes a standard plastic tube, a standard polytetrafluoroethylene tube, and a standard polyvinyl chloride tube.

Optionally, the optical pump includes a standard semiconductor laser, a standard laser diode, or a standard laser emitting diode.

Optionally, the frequency discriminator includes an interferometer or a second optical cavity. Optionally, the interferometer includes a Michelson interferometer or a Mach-Zehnder interferometer. The second optical cavity includes a Fabry-Perot resonator.

Optionally, detecting a respective frequency shift for each respective resonance with a frequency discriminator includes the following. A plurality of laser beams is transmitted through the single mode optical fiber, the laser beams comprising a plurality of respective laser frequencies, the plurality of laser beam frequencies being tuned to the plurality of respective resonances. Changes in the plurality of respective resonances are read out by the frequency discriminator 50 based on changes in transmitted or reflected laser beams from the plurality of optical cavities.

Another embodiment of the invention includes a method and is described as follows. A distributed feedback ("DFB") fiber laser acoustic emission sensor 110, for example, as shown by way of illustration in FIG. 1. The DFB fiber laser acoustic emission sensor 110 includes a fiber Bragg grating ("FBG"), typically a few millimeters to a few centimeters in length with a phase shift in the center, written into photosensitive erbium-doped fiber. The DFB fiber laser acoustic emission sensor 110 communicates with an optical pump 70, e.g., a standard laser. The laser is pumped at, for example, either 980 nm or 1480 nm. For example, the laser has a lasing threshold at, for example, typically less than 1 mW. The optical mode is centered at the phase shift in the FBG and falls exponentially on either side. This optical mode, typically ~5-10 mm in width, corresponds to the sensitive region of the laser sensor 110. The sensitive region of the DFB fiber laser acoustic emission sensor 110 is understood to be centered on the optical cavity.

To perform a measurement of acoustic emission ("AE") in a practical structure, the fiber laser sensor 110 is integrated into a grove in a panel or on the surface of a structure under test, in an embodiment of the invention. In another embodiment of the invention, a collar is optionally fitted onto a curved structure, such as a tube or a pipe, wherein the collar itself includes the groove. The fiber laser sensor is adhered to the groove, for example, with grease. When a crack forms, an AE signal is generated from the release of energy. This AE signal generates axial strain in the cavity of the DFB fiber laser sensor 110, which modulates the frequency of the laser. For example, the DFB fiber laser acoustic emission sensor 110 includes the optical pump 70 and the single mode optical fiber 10. The frequency shift of the fiber laser sensor 110 is decoded with a standard frequency discriminator 50 (e.g., a standard fiber optic interferometer), located remotely from the fiber laser sensor, as shown by way of illustration in FIGS. 1 and 11.

In an alternative embodiment of the invention, multiple lasers are multiplexed along a single mode optical fiber providing multipoint measurement. The single mode optical fiber in such an alternative embodiment includes multiple respective optical cavities, i.e., optical cavities 1 to N, as shown by way of illustration in FIG. 1. The multiple respective optical cavities correspond to the wavelengths of the multiple lasers or multiple laser beams. In other words, such a single mode optical fiber includes a standard chirped fiber Bragg grating structure with small (i.e., on the order of millimeters) spacing between optical cavities, each optical cavity being its own laser sensor, for example, as discussed in R. Slavik, I. Castonguay, S. LaRochelle, Member, IEEE, and S. Doucet, "Short Multiwavelength Fiber Laser Made of a Large-Band Distributed Fabry-P rot Structure" IEEE Photonics Technology Letters, Vol. 16, NO. 4, April 2004, which is incorporated herein by reference.

In an alternative embodiment of the invention, standard phased array beamforming is used for event location, e.g., the location of the source of a crack. Phased array beamforming is, for example, implemented using a standard time shift and sum method or using standard frequency domain techniques, such as a two-dimensional Fourier transform. For example, one of ordinary skill in the art will readily appreciate that phased array beamforming in transmission provides bearing of forward scattered signals. As another example, one of ordinary skill in the art will also readily appreciate that phased array beamforming in reflection provides bearing and range of backscattered signals from the defect or damage.

Although a particular feature of the disclosure may have been illustrated and/or described with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

This written description sets forth the best mode of the invention and provides examples to describe the invention and to enable a person of ordinary skill in the art to make and use the invention. This written description does not limit the invention to the precise terms set forth. Thus, while the invention has been described in detail with reference to the examples set forth above, those of ordinary skill in the art may effect alterations, modifications and variations to the examples without departing from the scope of the invention.

These and other implementations are within the scope of the following claims.

What is claimed as new and desired to be protected by Letters Patent of the United States is:

1. A method comprising:
adhering a single mode optical fiber to a structure, the single mode optical fiber comprising a first optical cavity, the first optical cavity comprising two fiber Bragg gratings with a distance therebetween, the first optical cavity comprising a resonance;
measuring a frequency shift of the resonance of the first optical cavity with frequency discriminator; and
detecting an acoustic emission from the structure based on the frequency shift,
wherein the single mode optical fiber comprising an optical gain medium,
wherein the method further comprises:
exciting the optical gain medium using an optical pump, thereby generating lasing in the optical cavity.

2. The method according to claim 1, wherein the optical gain medium comprises one of an erbium doped optical gain medium and a neodymium-doped optical gain medium.

3. The method according to claim 1, wherein the optical pump comprises an optical wavelength,
wherein the first optical cavity comprises an optical cavity width, the optical cavity width being about a multiple of half of the optical wavelength.

4. The method according to claim 1, wherein said adhering a single mode optical fiber to a structure comprises using one of a viscous liquid and an adhesive to impedance-match the single mode optical fiber to the structure.

5. The method according to claim 4, wherein the viscous liquid comprises one of gel and grease.

6. The method according to claim 1, wherein said adhering a single mode optical fiber to a structure comprises:
enclosing the single mode optical fiber in a viscous-liquid-filled tube.

7. The method according to claim 6, wherein the viscous-liquid-filled tube comprises one of a plastic tube, a polytetrafluoroethylene tube, and a polyvinyl chloride tube.

8. The method according to claim 1, wherein the optical pump comprises one of a semiconductor laser, a laser diode, and a light emitting diode.

9. The method according to claim 1, wherein the frequency discriminator comprises one of an interferometer and a second optical cavity.

10. The method according to claim 9, wherein the interferometer comprises a Michelson interferometer and a Mach-Zehnder interferometer,
wherein the second optical cavity comprises a Fabry-Perot resonator.

11. The method according to claim 1, further comprising transmitting a laser beam through the single mode optical fiber, the laser beam comprising a laser beam frequency, the laser beam frequency is tuned to the resonance of the first optical cavity; and
reading out changes in the resonance of the first optical cavity based on changes in one of transmitted and reflected laser beam from the first optical cavity.

12. A method comprising:
adhering a single mode optical fiber to a structure, the single mode optical fiber comprising a plurality of optical cavities tuned to respective optical frequencies, each optical cavity of the plurality of optical cavities comprising two fiber Bragg gratings with a distance therebetween, said each optical cavity of the plurality of optical cavities comprising a respective resonance;
the structure comprising an acoustic wavelength;
detecting a respective frequency shift for each respective resonance with a frequency discriminator;
detecting a plurality of respective acoustic emissions from the structure, each respective acoustic emission of the plurality of acoustic emissions being based on each respective frequency shift; and determining a direction of an acoustic emissions source by applying phased array processing to the plurality of respective acoustic emissions, wherein the plurality of optical cavities comprises an optical cavity spacing, the optical cavity spacing being about half of the acoustic waveleneth.

13. The method according to claim 12, wherein the single mode optical fiber comprising an optical gain medium, wherein the method further comprises:

exciting the optical gain medium using an optical pump, thereby generating lasing in the optical cavity.

14. The method according to claim 13, wherein the optical gain medium comprises one of an erbium-doped optical gain medium and a neodymium-doped optical gain medium.

15. The method according to claim 12, wherein said adhering a single mode optical fiber to a structure comprises using one of a viscous liquid and an adhesive to impedance-match the single mode optical fiber to the structure.

16. The method according to claim 15, wherein the viscous liquid comprises one of gel and grease.

17. The method according to claim 12, wherein said adhering a single mode optical fiber to a structure comprises:

enclosing the single mode optical fiber in a viscous-liquid-filled tube.

18. The method according to claim 17, wherein the viscous-liquid-filled tube comprises one of a plastic tube, a polytetrafluoroethylene tube, and a polyvinyl chloride tube.

19. The method according to claim 14, wherein the optical pump comprises one of a semiconductor laser, a laser diode, and a laser emitting diode.

20. The method according to claim 12, wherein the frequency discriminator comprises one of an interferometer and a second optical cavity.

21. The method according to claim 20, wherein the interferometer comprises a Michelson interferometer and a Mach-Zehnder interferometer, wherein the second optical cavity comprises a Fabry-Perot resonator.

22. The method according to claim 12, wherein said detecting a respective frequency shift for each respective resonance with a frequency discriminator comprises:

transmitting a plurality of laser beams through the single mode optical fiber, the laser beams comprising a plurality of respective laser frequencies, the plurality of laser beam frequencies being tuned to the plurality of respective resonances; and reading out changes in the plurality of respective resonances based on changes in one of transmitted and reflected laser beams from the plurality of optical cavities.

* * * * *